(12) United States Patent
Shavit et al.

(10) Patent No.: US 9,011,293 B2
(45) Date of Patent: Apr. 21, 2015

(54) METHOD AND SYSTEM FOR MONITORING AND FEED-BACKING ON EXECUTION OF PHYSICAL EXERCISE ROUTINES

(75) Inventors: Arie Shavit, Herzeliya (IL); Idit Perl Shavit, Herzeliya (IL); Alon Shavit, Rishon-le-Zion (IL)

(73) Assignee: Flow-Motion Research and Development Ltd., Herzeliya (IL)

( * ) Notice: Subject to any disclaimer, the term of this patent is extended or adjusted under 35 U.S.C. 154(b) by 413 days.

(21) Appl. No.: 13/359,273

(22) Filed: Jan. 26, 2012

(65) Prior Publication Data

US 2012/0190505 A1 Jul. 26, 2012

Related U.S. Application Data

(60) Provisional application No. 61/436,402, filed on Jan. 26, 2011.

(51) Int. Cl.
*A63B 71/00* (2006.01)
*A63B 24/00* (2006.01)
(Continued)

(52) U.S. Cl.
CPC ........ *G09B 19/0038* (2013.01); *A63B 71/0622* (2013.01); *A63B 21/0724* (2013.01); *A63B 24/0006* (2013.01); *A63B 24/0075* (2013.01); *G06F 3/011* (2013.01); *G06F 3/017* (2013.01); *G06F 3/0304* (2013.01); *G06F 19/3481* (2013.01); *A63B 2024/0015* (2013.01); *A63B 2071/0647* (2013.01); *A63B 2071/068* (2013.01); *A63B 2220/10* (2013.01); *A63B 2220/803* (2013.01); *A63B 2225/20* (2013.01);
(Continued)

(58) Field of Classification Search
CPC .................. A63B 2220/05; A63B 2024/0012; A63B 2024/0006; A63B 2024/0071
USPC .......................... 482/1, 5, 8–9; 434/256, 257
See application file for complete search history.

(56) References Cited

U.S. PATENT DOCUMENTS 6,774,885 B1 8/2004 Even-Zohar
8,488,888 B2 * 7/2013 Balan et al. ................... 382/224
(Continued)

FOREIGN PATENT DOCUMENTS

CN 101912676 A 12/2010
CN 201815058 U 5/2011
(Continued)

*Primary Examiner* — Loan H Thanh
*Assistant Examiner* — Sundhara Ganesan
(74) *Attorney, Agent, or Firm* — M&B IP Analysts, LLC

(57) ABSTRACT

A system for monitoring performance of a physical exercise routine comprises a Pilates exercise device enabling a user to perform the physical exercise routine, a plurality of motion and position sensors for generating sensory information that includes at least position and movements of a user performing the physical exercise routine; a database containing routine information representing at least an optimal execution of the physical exercise routine; a training module configured to separate from sensory information at least appearance of the Pilates exercise device, compare the separated sensory information to the routine information to detect at least dissimilarities between the sensory information and the routine information, wherein the dissimilarities indicate an incorrect execution of the physical exercise routine, the training module is further configured to feedback the user with instructions related to correcting the execution of the physical exercise routine by the user; and a display for displaying the feedback.

18 Claims, 17 Drawing Sheets

(51) Int. Cl.

| | | |
|---|---|---|
| *G09B 19/00* | (2006.01) | |
| *A63B 71/06* | (2006.01) | |
| *G06F 3/01* | (2006.01) | |
| *G06F 3/03* | (2006.01) | |
| *A63B 21/072* | (2006.01) | |
| *G06F 19/00* | (2011.01) | |

(52) U.S. Cl.
CPC ......... *A63B2225/50* (2013.01); *A63B 2230/06* (2013.01); *A63B 2230/30* (2013.01); *A63B 2243/0004* (2013.01); *A63B 2243/0025* (2013.01); *A63B 2243/0029* (2013.01); *A63B 2243/0037* (2013.01); *A63B 2243/0066* (2013.01)

(56) References Cited

U.S. PATENT DOCUMENTS

| | | | |
|---|---|---|---|
| 2002/0002103 A1 | 1/2002 | Watterson et al. | |
| 2003/0151554 A1 | 8/2003 | McCarthy | |
| 2004/0248071 A1 | 12/2004 | Bedziouk et al. | |
| 2005/0223799 A1* | 10/2005 | Murphy | 73/510 |
| 2005/0239026 A1* | 10/2005 | Suzuki et al. | 434/251 |
| 2005/0288159 A1 | 12/2005 | Tackett | |
| 2006/0073449 A1 | 4/2006 | Kumar et al. | |
| 2006/0217233 A1 | 9/2006 | Lee | |
| 2006/0235643 A1* | 10/2006 | Tokuyama | 702/150 |
| 2007/0219059 A1 | 9/2007 | Schwartz et al. | |
| 2007/0219744 A1* | 9/2007 | Kolen | 702/150 |
| 2007/0225118 A1 | 9/2007 | Giorno | |
| 2007/0275830 A1 | 11/2007 | Lee et al. | |
| 2008/0015089 A1 | 1/2008 | Hurwitz et al. | |
| 2008/0119332 A1 | 5/2008 | Roman | |
| 2008/0242437 A1* | 10/2008 | Taylor | 473/269 |
| 2009/0042695 A1* | 2/2009 | Chien et al. | 482/1 |
| 2009/0259148 A1* | 10/2009 | Willmann et al. | 600/595 |
| 2009/0270193 A1* | 10/2009 | Stremmel et al. | 473/55 |
| 2009/0298650 A1 | 12/2009 | Kutliroff | |
| 2009/0299232 A1* | 12/2009 | Lanfermann et al. | 600/595 |
| 2009/0326341 A1* | 12/2009 | Furlan | 600/301 |
| 2010/0015585 A1* | 1/2010 | Baker | 434/247 |
| 2010/0022351 A1* | 1/2010 | Lanfermann et al. | 482/1 |
| 2010/0041498 A1* | 2/2010 | Adams | 473/451 |
| 2010/0120537 A1* | 5/2010 | Yamaoka et al. | 463/42 |
| 2010/0145232 A1* | 6/2010 | Jang et al. | 600/587 |
| 2010/0173276 A1 | 7/2010 | Vasin | |
| 2010/0195869 A1 | 8/2010 | Geiss | |
| 2010/0197399 A1 | 8/2010 | Geiss | |
| 2010/0208945 A1* | 8/2010 | Te Vrugt et al. | 382/107 |
| 2010/0222179 A1 | 9/2010 | Temple et al. | |
| 2010/0234699 A1* | 9/2010 | Lanfermann et al. | 600/301 |
| 2010/0246898 A1* | 9/2010 | Izumi | 382/106 |
| 2010/0280418 A1* | 11/2010 | Klose | 600/595 |
| 2011/0006926 A1* | 1/2011 | Kim et al. | 341/20 |
| 2011/0072457 A1* | 3/2011 | Lanfermann et al. | 725/34 |
| 2011/0082007 A1 | 4/2011 | Birrell et al. | |
| 2011/0105278 A1 | 5/2011 | Fabbri et al. | |
| 2011/0124445 A1* | 5/2011 | Uehling, III | 473/461 |
| 2011/0172060 A1 | 7/2011 | Morales et al. | |
| 2011/0275042 A1 | 11/2011 | Warman et al. | |
| 2011/0306468 A1* | 12/2011 | Wilson et al. | 482/8 |

FOREIGN PATENT DOCUMENTS

| | | |
|---|---|---|
| WO | 8806776 A | 9/1998 |
| WO | 200116855 A2 | 3/2001 |
| WO | 2005021107 A | 3/2005 |
| WO | 2009074942 A | 6/2009 |
| WO | 2010102037 A2 | 9/2010 |
| WO | 2010145896 A | 12/2010 |

* cited by examiner

METHOD AND SYSTEM FOR MONITORING AND FEED-BACKING ON EXECUTION OF PHYSICAL EXERCISE ROUTINES

CROSS REFERENCE TO RELATED APPLICATIONS

This application claims the benefit of U.S. provisional application No. 61/436,402 filed on Jan. 26, 2011, the contents of which are herein incorporated by reference.

TECHNICAL FIELD

The present invention relates generally to techniques for tracking motions of an athlete performing physical exercise procedures.

BACKGROUND OF THE INVENTION

Recently developed game consoles include sensors for tracking a game player playing an electronic game. The sensors, in part, identify the player's body position and motion in space. One example is "Kinect®" which is integrated in a XBOX 360® gaming console provided by Microsoft® Corporation.

The motion and position sensors identify and track the position and movements of a player and are provided as inputs to the controller of the electronic game. The controller, based on such inputs, executes the game scenes (e.g., performs actions by the game's characters) or allows a player to change the game's setting by browsing through menus. Thus, such motion and position sensors enhance the overall gaming experience.

Conventional motion and position sensors utilized in game consoles generate an output in a form of a "skeletal model." As schematically illustrated in FIG. 1, a skeletal model 100 is a collection of joints 110 and lines 120 representing the body bones connected. The model's output is a data structure that includes coordinates describing the location of the joints and connected lines of a human body's bones. An example for skeletal model representation and generation thereof can be found in US Patent Application Publication US 2010/0197399 to Geiss, referenced herein merely for the useful understanding of the background.

The outputs generated by the sensors are merely utilized by a game controller to control the game. Existing game consoles or other devices that utilize the inputs from the sensors do not provide any means for identifying a motion routine performed by a user and do not provide feedback with regard to the execution of such a routine. Thus, there is no conventional device, disclosed in the related art, that utilizes motion and position sensors information, to identify a physical exercise routine performed by, for example, a gymnast, to analyze the gymnast's performance, and provide a feedback as to how the gymnast should improve the routine.

SUMMARY OF THE INVENTION

Certain embodiments include herein include a method and system for monitoring performance of a physical exercise routine. The system comprises a Pilates exercise device enabling a user to perform the physical exercise routine, a plurality of motion and position sensors for generating sensory information that includes at least position and movements of a user performing the physical exercise routine; a database containing routine information representing at least an optimal execution of the physical exercise routine; a training module configured to separate from sensory information at least appearance of the Pilates exercise device, compare the separated sensory information to the routine information to detect at least dissimilarities between the sensory information and the routine information, wherein the dissimilarities indicate an incorrect execution of the physical exercise routine, the training module is further configured to feedback the user with at least instructions related to correcting the execution of the physical exercise routine by the user; and a display for displaying the feedback.

BRIEF DESCRIPTION OF THE DRAWINGS

The subject matter that is regarded as the invention is particularly pointed out and distinctly claimed in the claims at the conclusion of the specification. The foregoing and other features and advantages of the invention will be apparent from the following detailed description taken in conjunction with the accompanying drawings.

DETAILED DESCRIPTION OF THE INVENTION

Figure 1:
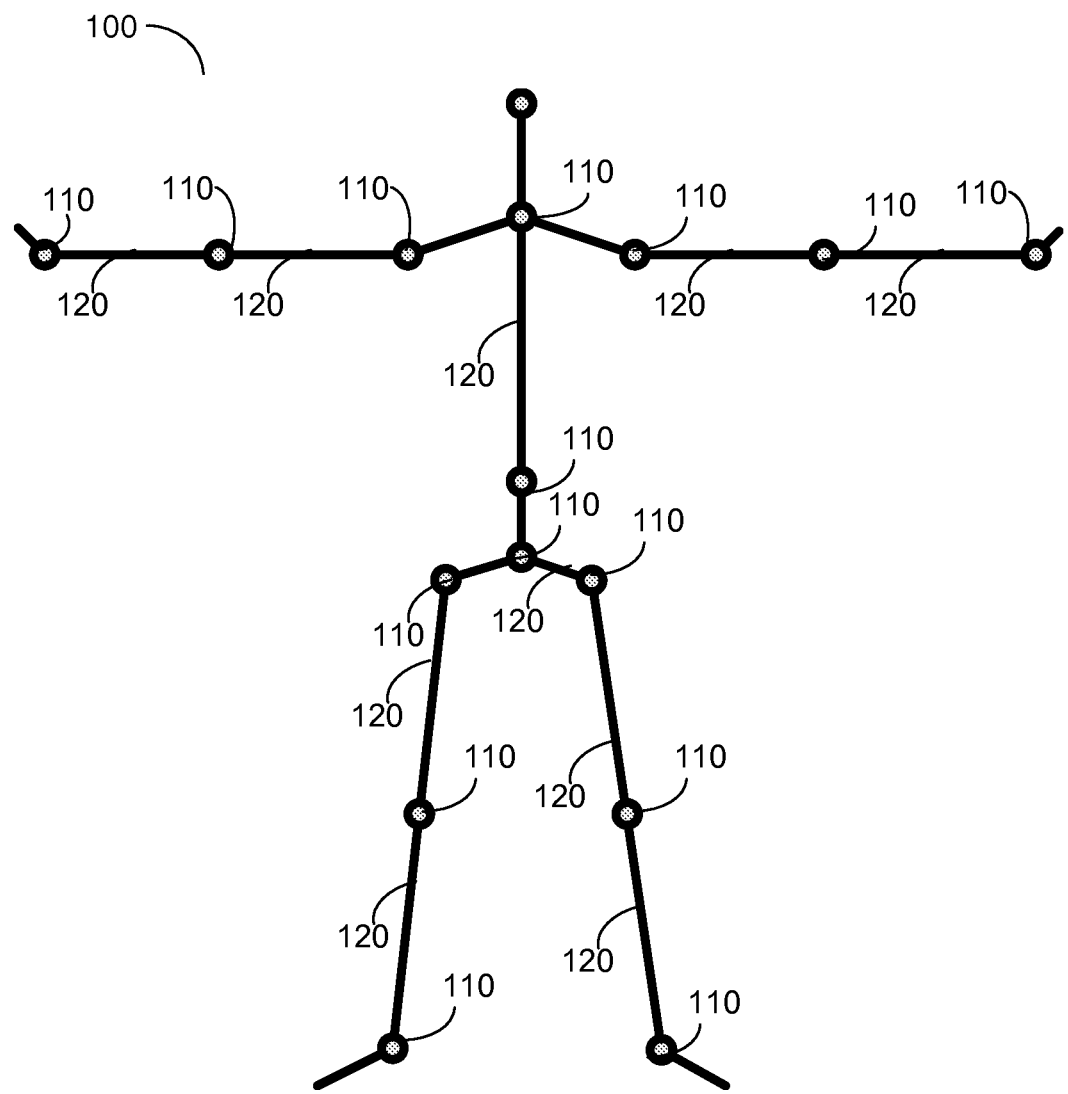
FIG. 1 is a visual representation a skeletal model.

It is important to note that the embodiments disclosed are only examples of the many advantageous uses of the innovative teachings herein. In general, statements made in the specification of the present disclosure do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

Figure 2:
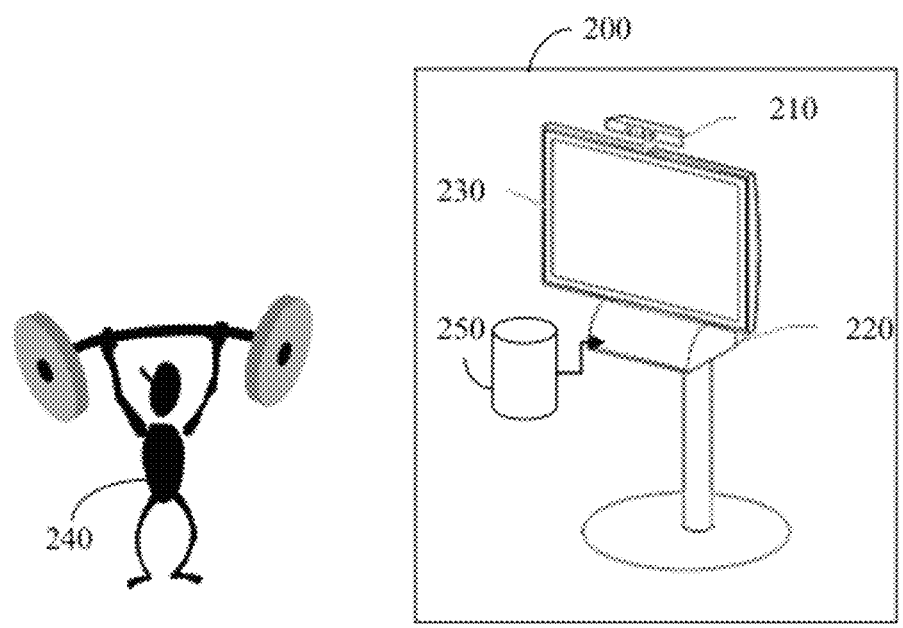
FIG. 2 is a diagram of a system for identifying and monitoring the performance of a physical exercise routine according to an embodiment of the invention.

FIG. 2 is an exemplary and non-limiting diagram of a system 200 for identifying and monitoring the performance of a physical exercise routine according to an embodiment of the invention. The system 200 includes an array of motion and position sensors 210 connected to a training module 220, and a display 230. The system 200 may also include a database 250.

In the arrangement illustrated in FIG. 2, the system 200 monitors the performance of a user 240. The user 240, in an embodiment, is a gymnast performing physical exercise routines including, but not limited to, weight lifting, Pilates, Yoga, running, dancing, and so on. The user 240 may be also a ball-game player, such as a baseball player, a basketball player, a football player, a soccer player, a golf player, and the like, where the system 200 is utilized to provide clinic training for such players. It should be appreciated that the system 200 may also monitor and evaluate routines related to, for example, training procedures for medical teams, military training, monitoring performance of procedures performed by employees, and so on. It should be further appreciated that the system 200 can be utilized to monitor animals (e.g., dog training), or operation of machines, e.g., robots.

The sensors 210 generate an output with regard to at least the position and movements of the user 240 in the space. In an embodiment, the sensors' 210 outputs are generated and represented according to the skeletal model described above. The sensors 210 are positioned in the system 200 in a way that enables them to capture the entire body of the user 240 or a portion of the body depending on the physical exercise routine performed by the user 240. The display 230 may be, for example, a flat screen TV, a projector, a monitor, a touch screen, and the like.

The training module 220 is connected to the sensors 210 and the display 230 by means of a wire connection, a wireless connection, or combination thereof. Such connections can be realized through a USB, a HDMI, a DisplayPort, a Bluetooth, ZigBee, a communication standard and/or a network connection such as a local area network (LAN), a wireless LAN, and the like.

In an embodiment, the training module 220 and the display 230 are integrated in a single device. In this embodiment, the training module 220 can be realized as a laptop computer, a personal computer, a tablet computer, a smart phone, and the like. In other embodiment, the processing tasks performed by the training module 220 are carried by a server connected in the Web or a Cloud server. Thus, such a server is the training module configured to process information of multiple users. The sensor inputs can be provided to the server over the Internet.

Figure 12:
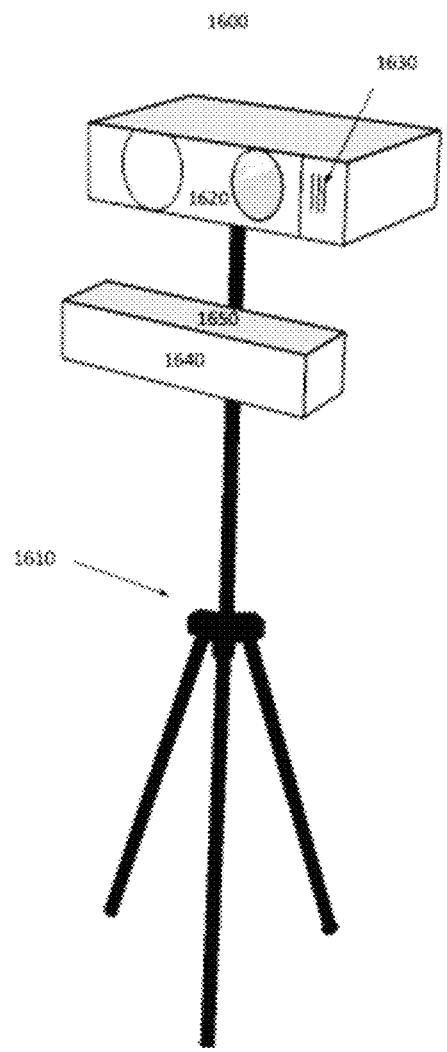
FIG. 12 is an exemplary arrangement of a mobile system for monitoring the execution of a physical exercise routine.

In an exemplary arrangement illustrated in FIG. 12, the system is a mobile system. In such an arrangement, the array of sensors 1620 is placed on a retractable tripod 1610 and the training module 1650 may be, e.g., a smart phone, or any portable device that includes or does not include a display. Such arrangement may also include training a sound subsystem (microphones 1630 and speakers 1640). The processing tasks in such an arrangement are performed, in part, by a server as discussed above, wherein sensory information is sent over the network to the server by the training module 1650.

According to certain embodiments, the training module 220 performs the tasks related to identifying the physical exercise routine performed by the user 240, monitoring the user's 240 performance with regard to the executed routine, and providing a feedback to the user as to how to improve the execution of the routine. For example, the feedback may include increasing the speed, performing a certain motion in a different way, and so on. The feedback may be displayed on the display 230 as text instructions, voice commands, and/or a video clip showing the user's performance and indications as to how the routine execution should be corrected.

In another embodiment, the training module 220 may display to the user step-by-step instructions on how to perform a certain physical exercise routine. Thus, the training module 220 acts as a virtual couch or trainer where physical exercise routines are presented to the user 240, and their executions are monitored. The training module 220 suggests corrections to the user's 240 movements and/or provides additional physical exercise routines as the user 240 advances in skill.

As will be described in detail below, as part of the monitoring of a routine execution, the training module 220 examines the position of a user and the position of a user's 240 movements by tracking body parts during various stages of the execution of the exercise routine, tracks the rate of movements, and counts the number of routine repetitions. For example, a physical exercise routine could be an arm exercise that requires the user to grip weights with her/his palms facing upward and curl the weights up toward her/his shoulders, and then back down again, during a 10 second period. This routine should be repeated 15 times. According to the disclosed embodiment, the training module 220 tracks the arms and shoulders of the user making sure that the execution of the routine is perfected, tracks the time it takes the user to complete the routine, counts the number of repetitions up to 15, and then instructs the user to stop.

It should be noted that the training module 220 can use additional inputs, other than the sensory information provided by the sensors 210, to evaluate the performance and to generate the feedback, using for example, the weight and age of the user, heart beat rate, and speed, to determine burnt calories, and so on. Such an input may be computed by the training module 220 or provided by an external resource, e.g., a heart rate measurement device.

According to certain embodiments, the training module 220 includes a processing unit coupled to a memory (both are not shown) that includes executable code to perform one or more of the tasks described herein. The memory may be in any form or non-transitory readable medium.

The database 250 may be integrated in, or externally connected to the module training module 220. The database 250 maintains the physical exercise routines, the inputs from the sensors 210, including, but not limited to, body position (may also be referred to as the body pose/posture) and/or configuration at one or more points throughout the routine. The database 250 may also include locations of joints relevant to the specific exercise at one or more poses throughout the exercise, angles of the body parts relative to the joints, or relative to other body parts or another point of relativity at one or more poses throughout the exercise, the length and/or forms of body parts and/or orientation and/or any other data describing body parts or body parts' attributes at one or more poses throughout the exercise.

The saved body poses and/or positions can define a physical exercise routine and enable identification of it and/or monitoring of it. If, for example, the exercise is a physical exercise of bending and stretching the arms, one of these saved poses can be a position in which the arms are bent. Another saved position can be when the arms are stretched. For recognizing or monitoring of this physical exercise routine the module 220 can compare the input body positions to these stored body positions.

The database 250 also includes a recommended time for moving from one body pose to another body pose, to monitor of the pace of exercises' execution; the time of staying in a posture, i.e., if the exercise requires staying in a static posture for some time; the attributes of the exercise to monitor, and/or the best viewing position and angle for the sensor system for a specific exercise or group of exercises and more. The database 250 may also include voice recognition entries mapping an exercise plan to a user (e.g., a user 240 will be able to choose an exercise by saying its name), or for a physical exercise routine by saying its name, the database 250 may also include physiological data, such as recommended heart rate range, blood pressure, and so on.

Figure 3:
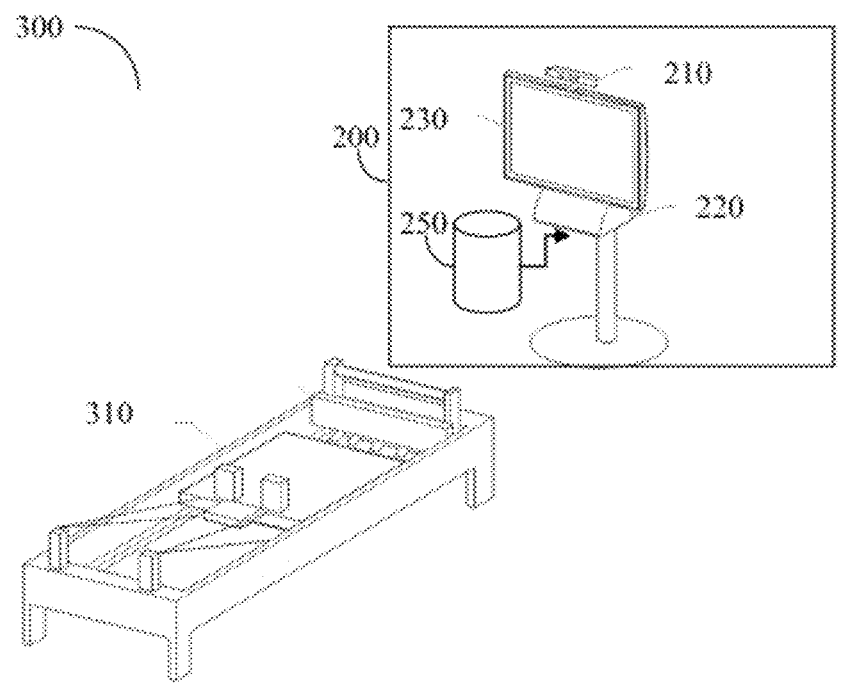
FIG. 3 is a diagram showing an arrangement of the disclosed system in a Pilates exercise device according to one embodiment.

FIG. 3 shows an exemplary arrangement of the system 300 according to another embodiment of the invention. The array of motion and position sensors 210 are mounted on a Pilates exercise device 310. The device 310 may be any type of Pilates exercise device including, but not limited to, a Reformer, a Pilates Chair, a Pilates Cadillac, and the like. The sensors 210 can adjust their viewing angle according to the movement of a user of the device 310.

The database 250 contains information about the location and optimal viewing angle for sensors 210 in the various Pilates physical exercise routines. The training module 220 adjusts the viewing angle of the sensors 210 based on the physical exercise routine being performed. Alternatively, the training module 220 may compute the optimum viewing angle and position the sensors 210 accordingly.

In an embodiment of the invention, the training module 220 can adjust the resistance of the device 310 based on the physical exercise routine being performed and information saved in the database 250. An example for a device in which its resistance can be electronically controlled is described in a co-pending US patent application "METHOD AND APPARATUS FOR ELECTRONICALLY CONTROLLED RESISTANCE IN EXERCISE EQUIPMENT" to Shavit, et al., filed on the same date as the present application, assigned to common assignee and hereby incorporated by reference.

In the embodiment shown in FIG. 3, one of the sensors 210 is a depth sensor being placed in a diagonal angle toward the front side of the device 310. Thus, the user lies in front of the depth sensor, and as a result of the movement being performed, in front of the majority of resistance, the depth axis allows efficient data gathering using this type of sensor. The depth sensor generates a skeletal model (image) that allows the training module 220 to identify, monitor, and provide feedback on the execution of a Pilates routine performed on the device 310. These tasks are further described below. The sensory information provided by the depth sensor can also be utilized to compute the calories burnt during the exercise based, in part, on the rate of change in the depth axis.

Figure 4:
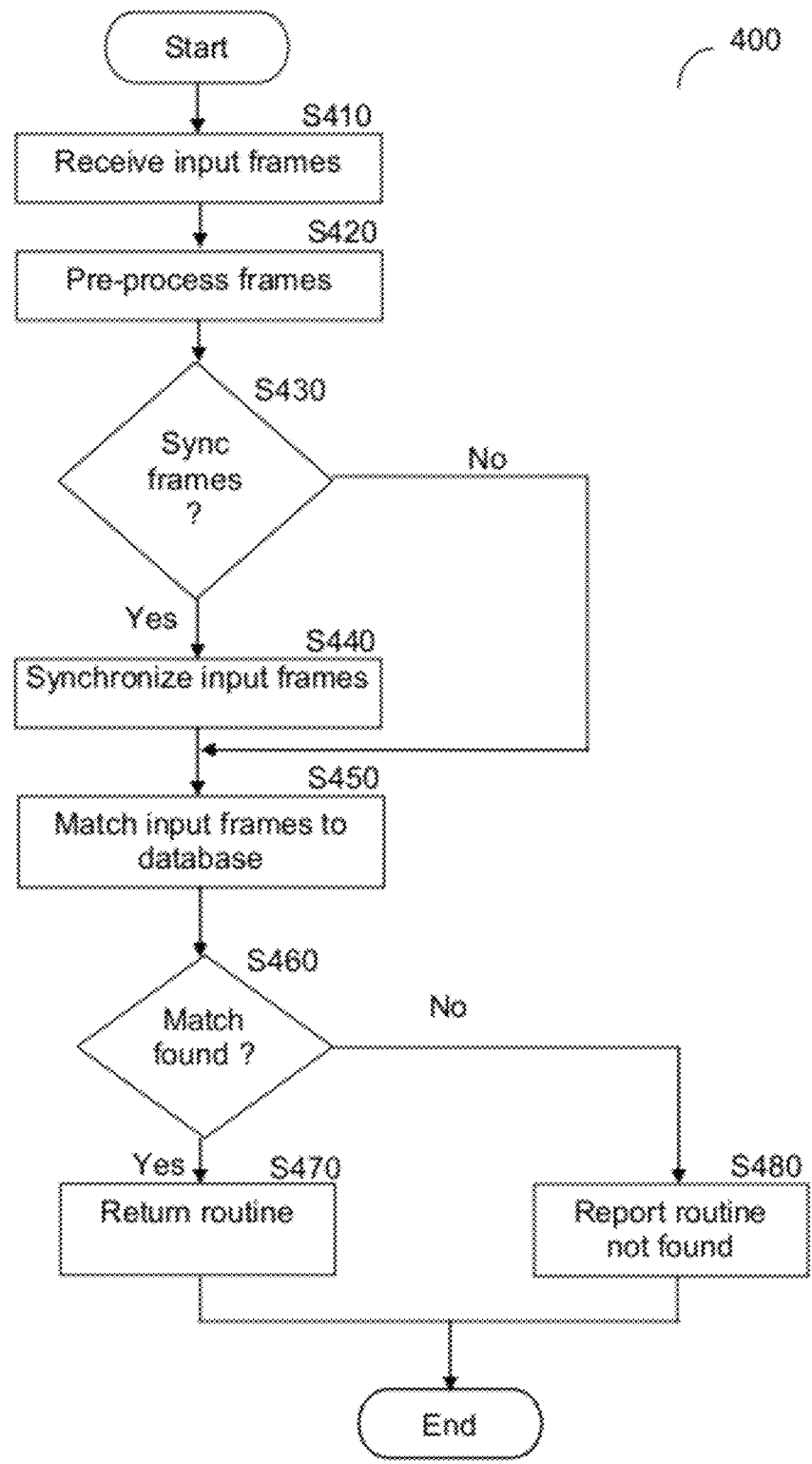
FIG. 4 is a flowchart of a method for identifying a physical exercise routine performed by a user according to one embodiment.

FIG. 4 is a non-limiting and exemplary flowchart 400 illustrating a method for identifying a physical exercise routine performed by the user according to an embodiment of the invention. To simplify the description of the method and without limiting the scope of the invention, the method will be described with reference to the system 200 illustrated in FIGS. 2 and 3.

At S410, input data is received from the array of motion and position sensors 210. According to an embodiment, the inputs are coordinates as generated by the skeletal model mentioned above. The input data may be included in a data structure that stores information about objects or location of body parts, such data structure is readable and can be processed by the training module 220. In another embodiment, the input may be in a raw form such as the sensory data, video data and/or depth image. The input data may also include information received from external devices monitoring, for example, heart rate, blood pressure, and the like.

Optionally, at S420, pre-processing of the received input data is performed. Step S420 may include at least one of: down sampling of the input data, converting the input data to a format that can be saved in the database 250, and reconstruction of missing or wrong body parts data required for processing by the method.

In an embodiment, the down sampling is performed by reducing the frames' rate or dropping some of the frames' input data. This allows reducing the processing time and bandwidth utilized by the training module 220. A frame may be an object that contains the position, pose, and/or posture of the tracked body parts, the body orientation, and/or other relevant data or states captured at a certain point in time. As a non-limiting example, a frame is a three dimensional picture of the tracked body that may be in one of the relevant formats and may be accompanied by relevant data to the specific captured time. The conversion task includes changing the input data to the format that complies with the data structured stored in the database 250. This task may also include performing lossless compression of the input data.

Yet another embodiment, of a down-sampling task may be performed by averaging a number of frames (for non-limiting example 5), saving the averaged results as representing these frames, and dropping the original frames. One of ordinary skill should be familiar with the several techniques of averaging frames.

In an embodiment, if a frame is represented by a skeletal model of the subject posture or a list of coordinate points, another pre-processing step that may be done is converting the input frame coordinates to the set of coordinates used for the processing. The embodiment can use Cartesian coordinates, Polar coordinates $(r, \theta, \phi)$ Cylindrical coordinates, and/or any linear transformation of these coordinates systems. In addition, skeletal representation using joints, bones, and the angles between the bones, can be utilized. One of ordinary skill should be familiar with the several techniques of how to transform from one coordinate system or representation to the other.

The reconstruction task includes identifying missing information related to body parts in the received input data. Once identified, the training module 220 reconstructs and adds the data in a format of the frames that missing body parts are processed. This can be achieved, for example, by averaging nearest neighbor frames or filtering information embedded in a frame. This task further includes reorganization of incorrect input data, and fixing or filtering such data. That is, input data that contains body parts which make them reach non-logic or unreachable poses/postures, can be filtered. For example, a leg bent forward across the knee so that the foot is in an angle pointing to the face, or a hand getting "into" the torso, and so on, can be corrected. As another example, input data that makes body parts travel in speeds above their possible limits or go through unreachable positions is also filtered. The recognition and filtering of such information can be performed using information stored in the database 250, for example, information regarding the limited distances that body parts can travel between frames, or definitions of unreachable postures. Correction of incorrect input data may be performed by considering, e.g., an incorrect location of a body part and adding or subtracting a "fix vector" in the required direction.

At S430, it is checked if synchronization of the input data with respective data stored in the database 250 is required. If so, execution continues with S440; otherwise, execution continues with S450. The input data and the database contain frames having a format described above. The determination of whether the synchronization is necessary is based on, for example, if a starting point of the physical exercise routine has been identified in the input data, whether the cycle of the exercise can be recognized from the input, whether the edge frames are recognized, and so on. In another embodiment, the determination of whether the synchronization process should be performed is based on a matching between the physical exercise routine performed (the input) and the respective routine saved in the database 250. If the degree of the matching is lower than a certain threshold, then the synchronization process is required. In another embodiment, the training module 220 may be configured to always perform S440 or not to perform S440, thus in this embodiment S430 is optional.

At S450, a synchronization process is performed for at least correlating the input frames to their respective frames or data structures saved in the database 250. In one embodiment, the synchronization process detects edge frames, in the input data. Such edge frames include body parts at their maximum movement position (e.g., hands spread to maximum, legs extended, arms bent to the maximum required in the exercise, etc.), to determine the starting position and end position of a physical exercise routine. The starting and end positions of a physical exercise routine are two edge frames. The two edge frames in the input data are matched against edge frames saved in the database 250. Thus, the database 250 is enabled to synchronize the frames in the input data to the frames in the database 250 to enable later identification of the physical exercise routine being performed.

In another embodiment, the synchronization process, based on the distance in terms of space and/or time for non-edge frames from edge frames, or from neighboring frames stored in the data base, can be calculated and stored in the database 250. Other parameters may be, for example, angles between two body parts, an angle relative to a joint, distance or angles relative to a point in space or another body, and so on. The input data can be synchronized by the same parameters or a combination of these parameters. The synchronization can be achieved from a neighboring frame which is already synchronized, or relative to an edge frame or starting/edge positions. This way, for example, frames from the input having similar parameters, such as distance of body parts relative to edge frames, can be marked as synchronized. Alternately, frames that have similar time differences between them as frames in the database, can be marked as synchronized and used for later comparison.

In another embodiment, S440 can be performed using indications from the user 240 for start/end positions or for edge positions. As an example, a user notifies the training module 220 that he/she is about to start the exercise using, for example, a voice command. The training module 220 can mark the pose right after the notification as a start position. In another embodiment, frames related to start/end positions can be marked by calculating the physical exercise routine cycle (e.g., in time, space, angle, any other periodic variable) based on examining several repetitions. It should be noted that S440 can be performed based on one or more of the embodiments described herein.

At S450, the input frames are compared to frames in the database 250 in order to recognize the physical exercise routine being performed. It should be noted that execution reaches S450 with a selection indication as to whether to select an input of unsynchronized frames (S410) or synchronized frames (S440).

Figure 5A:
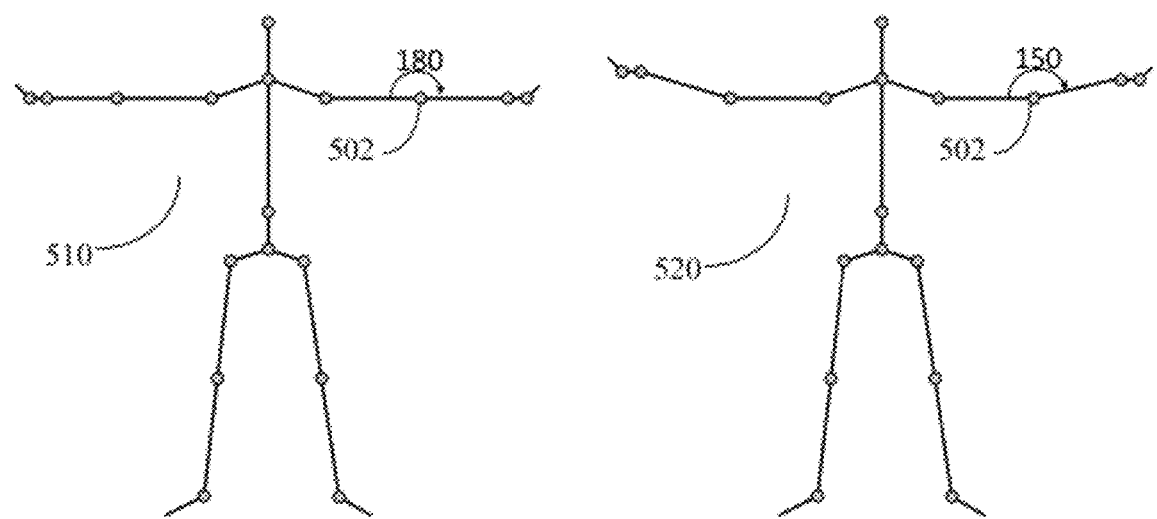
FIG. 5A is a diagram illustrating the comparison of two frames.

One embodiment to performing S450 is described with a reference to FIG. 5A. In this embodiment, the comparison is done according to the angle between two "bones" around a joint which serves as a vertex. As illustrated in FIG. 5A, the comparison will be performed between joints 501 and 502 in the exemplary input and database frames 510 and 520 respectively. Therefore, the method compares the angles around the relevant joints between two frames. Since the frame may describe positions and angels in three-dimensional space, there can be more than one angle per joint and more than one way to define the angles.

Figure 5B:
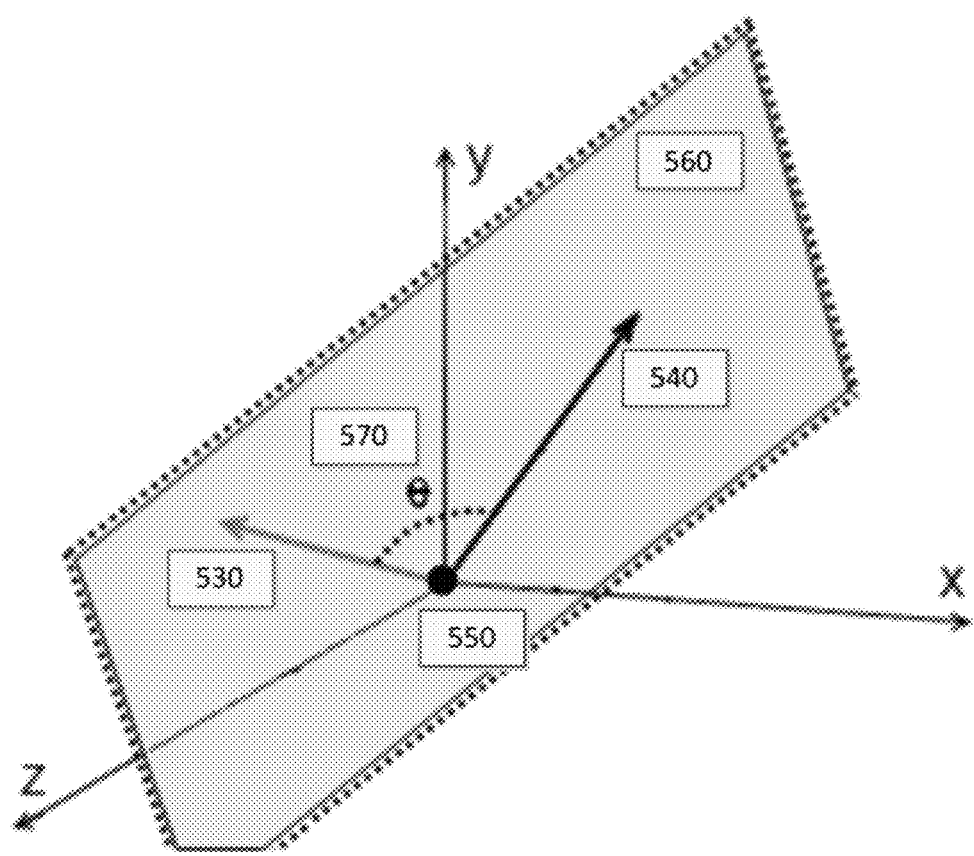
FIG. 5B is a diagram illustrating the computation of a difference in angles between two joints.

In a preferred embodiment, an angle between every two bones around a vertex joint is calculated and used for the comparison. This angle is depicted in FIG. 5B. The "bones" are depicted as vectors 530, 540. The joint is the vertex 550. According to a known theorem in Geometry, a surface can always be found that contains both lines that cross each other. This surface is 560. The angle formed on this surface, between the two lines, is the calculated angle 570. A rule can be set to make every angle measurement uniform, for example, the angle is always measured from left to right. This way it is easy to compare the two angles from different frames.

In another embodiment, at S450, the method compares the location of body parts between two or more frames. The location of the body part in each frame can be defined by a specific reference point on the body part, "Center of mass" of the part, the location of its selected edges, or locations of the joints.

The decision as to whether two frames are matched is based on a configurable threshold. For example, if certain attributes of the frames are equal or fall within the configurable threshold, then the frames are considered matched. If frames are considered matched, then a physical exercise routine associated with the respective frame stored in the database 250 is determined as the physical exercise routine being performed. As a non-limiting example, the attribute may be the angle between every two bones around the joints (as described above). If all these angles are equal or within a certain threshold from each-other, the frames can be considered equal. An attribute may also be the location of each joint.

In another embodiment, the decision as to whether the frames are matched is based on a statistical comparison process. According to this embodiment, the input frames (either from S410 or S440) are compared to the frames in the database 250. An entry in the database 250 describing the physical exercise routine which receives the highest comparison grade with respect to the input frames is determined as the identified physical exercise routine. In an embodiment, the comparison grade should exceed a configurable threshold.

The comparison grade can be computed as the sum or weighed sum of all comparison grades computed for individual input frames in the input stream. The comparison grade is computed by comparing a pivot frame to an input frame and the grade is determined based on the number of statistically matching attributes compared between the pivot frame and an input frame. The attributes may include the body part, location, angle, and so on.

As a non-limiting example, the comparison grade can be the sum of differences between the angles around joints as described above. The angle difference for a specific joint ($U_i$) may be computed as follows:

$$U_i = \theta_i - \phi_i$$

When $\theta_i$ is the angle around the joint as recorded in database 250 skeletal model and $\phi_i$ is the angle around the joint of an input frame represented as skeletal model, 'I' is an index running on the skeletal model joints.

The Comparison grade can be computed as follows:

$$G = \Sigma_{i=0}^{N} U_i = \Sigma_{i=0}^{N} (\theta_i - \phi_i)$$

Or;

$$G = \Sigma_{i=0}^{N} W_i U_i = \Sigma_{i=0}^{N} W_i (\theta_i - \phi_i)$$

When G is the comparison grade, $w_i$ is a weighting function, and T is the joints index. In one embodiment, each exercise can have its own weighting function; such function is saved in the database 250. As a non-limiting example, a weighting function can assign a high grade to angles around joints which are active in a given exercise routine (e.g., the grade can be 1), and a lower grade assigned to joints not active in a given exercise routine (e.g., 0.25 or 0).

It should be noted that an input frame can be matched against all frames in the database 250 or a sub-set of such frames. For example, if the physical exercise routine is a leg exercise, the input frame is matched against all frames that are associated with physical leg exercise routines.

At S460, a check is made to determine if S450 recognizes the physical exercise routine being performed, and if so, execution continues with S470 where the physical exercise routine is reported as detected and a message including the routine name/ID is generated; otherwise, at S480, a message is generated indicating that no physical exercise routine was found. The results of S450, S460, S470 and S480 may be further used for a future reference.

Figure 6:
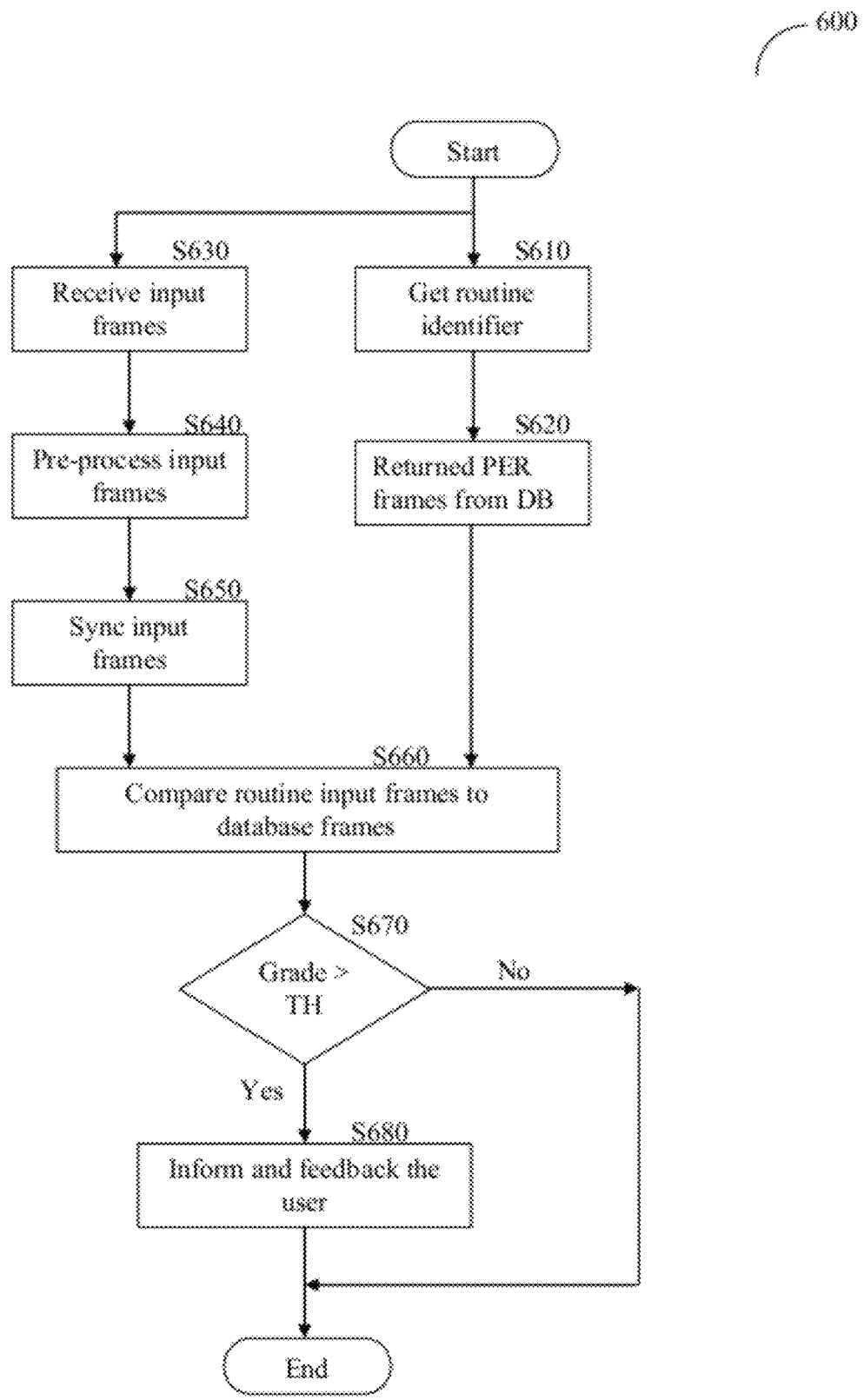
FIG. 6 is a flowchart illustrating a method for monitoring the execution of a physical exercise routine according one embodiment of the invention.

FIG. 6 shows an exemplary and non-limiting flowchart 600 describing the method for monitoring the execution of a physical exercise routine according to an embodiment of the invention. To simplify the description of the method and without limiting the scope of the invention, the method will be described with reference to the system 200 illustrated in FIGS. 2 and 3.

At S610, the name (or an identifier) of the physical exercise routine being performed is received. This input may be provided by the user 240 or by the identification method described in detail above with respect to FIG. 4. At S620, the physical exercise routine name is utilized to retrieve frames (or a data structure) associated with the physical exercise routine being performed.

At S630 input frames as captured by the sensors 210 are received. Such input may be in a format described in detail above. Optionally, at S640 and S650, the input frames are pre-processed and synchronized as described in detail with reference S420, S430, and S440 of FIG. 4.

At S660, the input frames are then compared to the specific physical exercise routine frames retrieved from the database 250. The input frames may be synchronized or unsynchronized. The comparison performed at S660 may be performed using one of more of the comparison embodiments described in detail above with reference to S450 of FIG. 4. However, in this embodiment, the comparison is performed in order to determine deviation of the input frames from the physical exercise routine frames. Specifically, in this embodiment, the method detects differences in one or more attributes (joint or body parts) in the frames. For example, as illustrated in FIG. 5, at S660 the differences between the angles around the elbow of the left hand is determined by comparing the angles around the elbows (joints 502 and 501) between the input frame 520 and a database frame 510.

Once dissimilarities with respect of the various attributes in the frames are detected, such dissimilarities are graded. For example, angle differences around the elbow which are 180 degrees and 150 degrees can be normalized to provide a grade representing the actual difference in degrees between the angles or the actual difference in the score (e.g., 30 degrees). Other embodiments for setting the grade can include multiplying the difference by a factor, computing a sum and not the difference, using non linear functions, emphasizing certain value ranges, and so on. The dissimilarities may be also categorized to different performance issues, for example, speed, pace, motion of the routine, and so on.

At S670, the dissimilarity grade is compared to a configurable threshold that determines the action that should be taken based on a crossing of such threshold. In an exemplary embodiment, if the grade is above the threshold, at S680 a feedback about the performance is provided to the user; otherwise, execution ends.

In another embodiment, the comparison step can give consideration to a configured tolerance in time. When dissimilarity is detected, then it is neither outputted nor saved in the database 250. The timestamp in which the frame was received is saved for the detected dissimilarity. This process is repeated for every subsequent frame, until the configured tolerance of the time period from the first detected dissimilarity has been elapsed. If within this time tolerance period a frame resulting in a match arrives, the detected dissimilarities together with their respective timestamps are discarded. On the other hand, if no frame resulting in a match arrives during the tolerance period, the dissimilarities are considered, and preferably saved and presented to the user.

The feedback may be a message displayed over a display 230 that the physical exercise routine is not being performed correctly and may include specific instructions as to how it should be corrected. For example, if the pace is two slow then a notification to increase the speed may be provided. As another example, if the arms are not fully spread, the feedback may include a message to stretch the arms together, for example, with a shot clip displayed over the display 230 as to how the routine should be performed. It should be appreciated that such feedback is computed based on the identified dissimilarities and the knowledge stored in the database 250 as to how the physical exercise routine should be performed. In an exemplary embodiment, a positive feedback may be provided if the physical exercise routine is perfectly executed. Such a positive feedback may include "good job" or a message encouraging the user to move to a harder routine. It should be noted that such feedback can be provided during the execution of a specific physical exercise routine or a set of physical exercise routines, or once the training is completed.

According to an embodiment of the invention, during an execution of a physical exercise routine the viewing angle sensors 210 can be adjusted so that the input frames will capture the body parts that are important to track for a specific physical exercise routine. It should be noted that once the physical exercise routine being performed is identified, the training module 220, based on the location and optimal viewing angle information associated with the physical exercise routine in the database 250, can adjust the sensor 220.

In addition to the optimal location and viewing angle respective to each physical exercise routine, the database 250 may be configured with the number of frames per second, or with which parts of the body should be tracked during the different stages of a physical exercise routine. This information can be used to optimize the performance of the system 200, given that the data bandwidth between the sensors 210 and training module 220 may be limited. In addition, it allows using fewer sensors 210 in the array. The training module 220 can also compute the optimal viewing angle and which body parts should be tracked once the physical exercise routine is identified.

For example, if a leg exercise is being performed, the training module 220 can first choose joints from the legs to track. If, for example, the number of joints that the sensors 210 can track is limited to a certain number, the module 220 can first select the leg joints including knees, hips, and ankles. If the all the selected leg joints do not reach the number of joints that can be tracked, the joints from nearby body parts, such as the back, are selected. Such selection orders can be configured in the database 250 or be performed during the execution of the routine. The selection of joints is transferred to sensors 210 by the module 220.

The selection of body parts to be tracked can be performed based on proximity to the area of interest. Accordingly, the areas or body parts closest to the area of interest are selected first, followed by selection of the next closest areas or parts until the limit is reached. Selection can also be performed based on a predefined priority assigned to each body part, based on the "participation" of the part in the physical exercise routine. For example, in an arm exercise that requires the user to grip weights with her/his palms facing upward and curl the weights up toward her/his shoulders, the selections of joints associated with the arm and shoulders should be selected first.

As can be understood from the above discussion, the database 250 contains valuable information for the execution of the various processes by the training module 220. Specifically, the database 250 includes a list of physical exercise routines that can be monitored, including for each physical exercise routine, a set of frames that represent perfect execution of the physical exercise routine, optimal location and viewing angle for the sensors 221, a list of body parts that should be monitored, and so on. Thus, according to certain embodiment, the content in the database 250 can be accessed by the user through an interface of the training module 220 or through an external computing device (not shown). The database 250 can be modified to add a physical exercise routine, edit certain features of a physical exercise routine, delete a physical exercise routine, and so on.

A physical exercise routine can be added to the database 250, for example, by uploading a file containing information related to the routine from an external source, e.g., a remote database including physical exercise routines. According to another embodiment, a physical exercise routine can be added to the database 250 by recording an actual execution of the physical exercise routine as performed by a certified user (e.g., a coach or a trainer). The input frames received from the input sensors 210 are saved by the training module 220 in the database 250. Then, the respective data structure can be edited to include additional information as associated with the physical exercise routine. Other embodiments for manipulating the content of the database 250 will be apparent to one of ordinary skill.

Following are some exemplary embodiments for the utilization of the system 300 that includes a Reformer device 310 as described in detail above with the reference to FIG. 3.

Figure 7A:
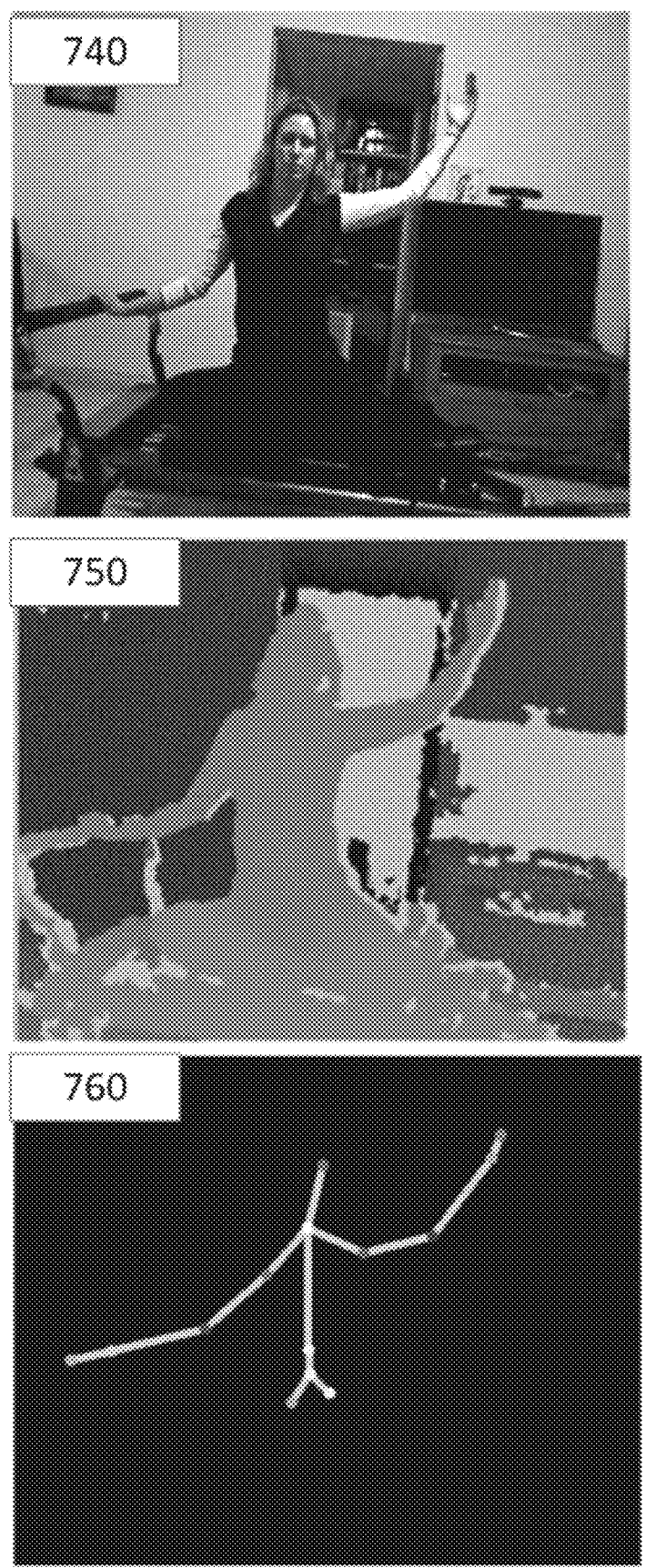
FIGS. 7A, 7B, 7C illustrate frames recorded during a Pilates exercise routine.
Figure 7B:
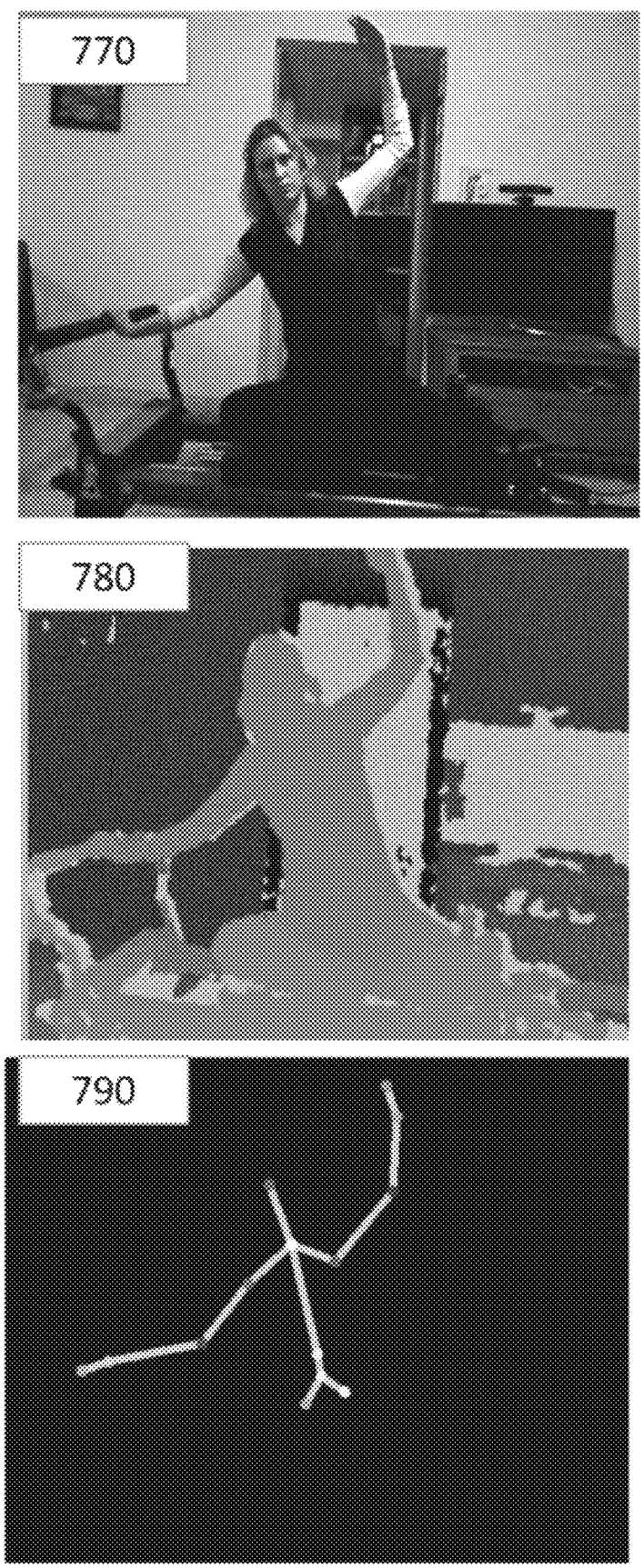
Figure 7C:
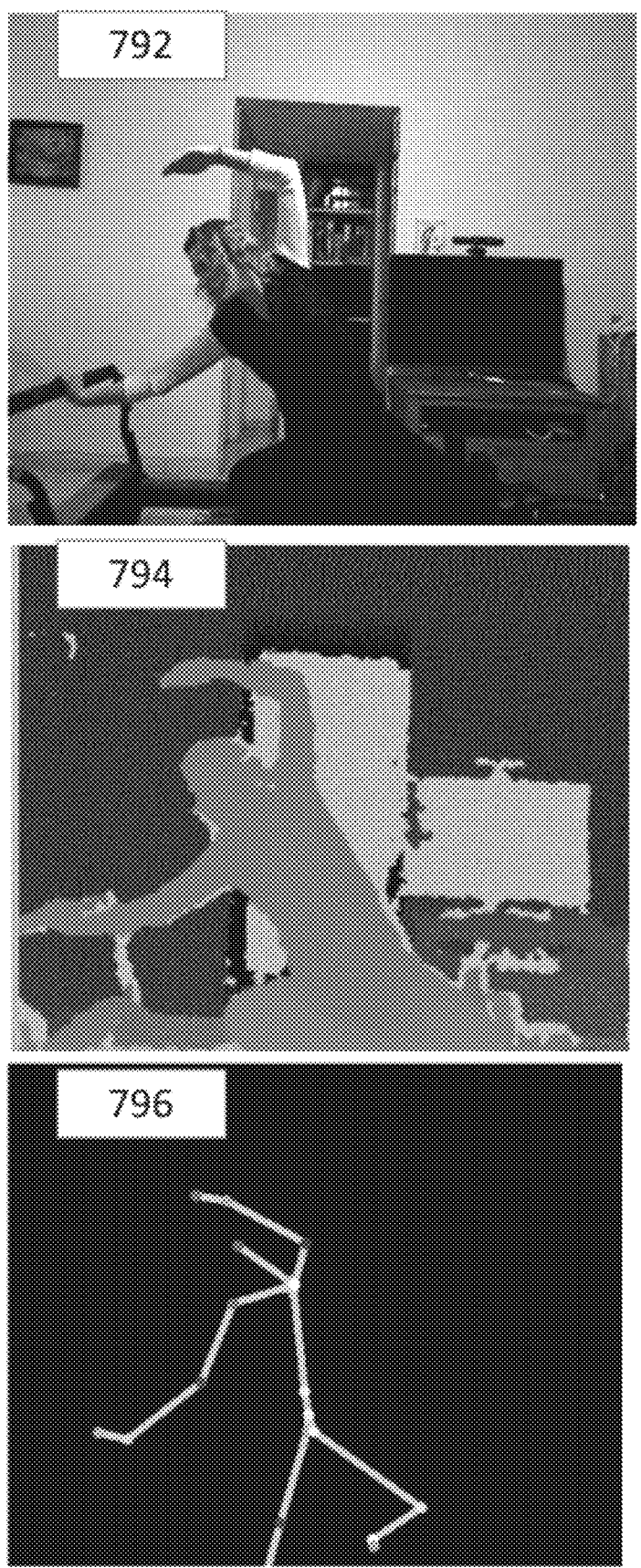
Figure 8:
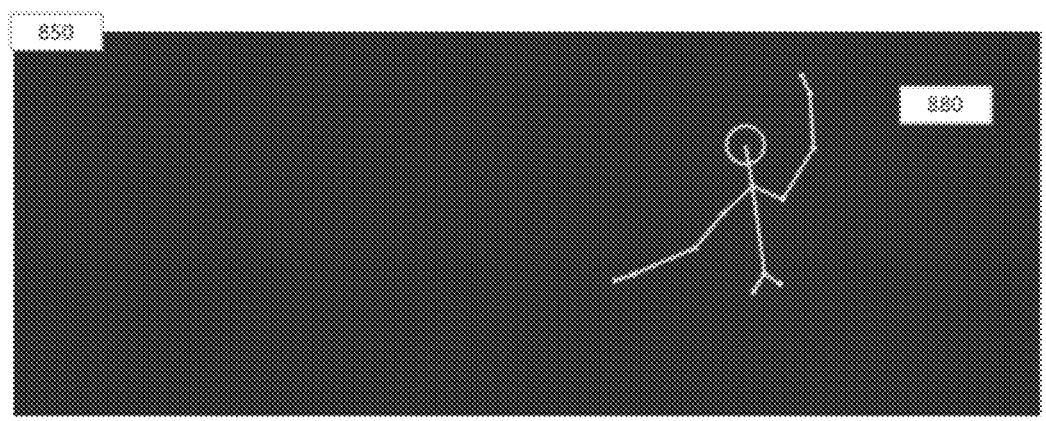
FIG. 8 shows exemplary screenshots taken from a recorder recording a Pilates exercise routine.
Figure 8:
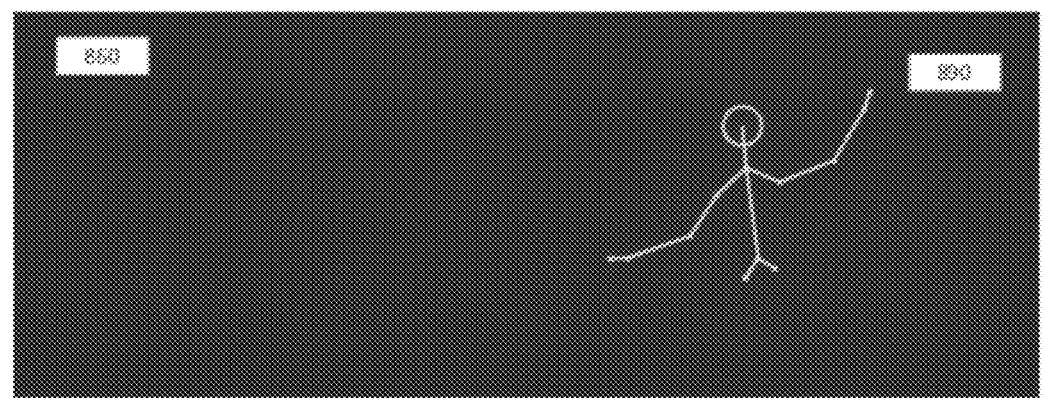
Figure 8:
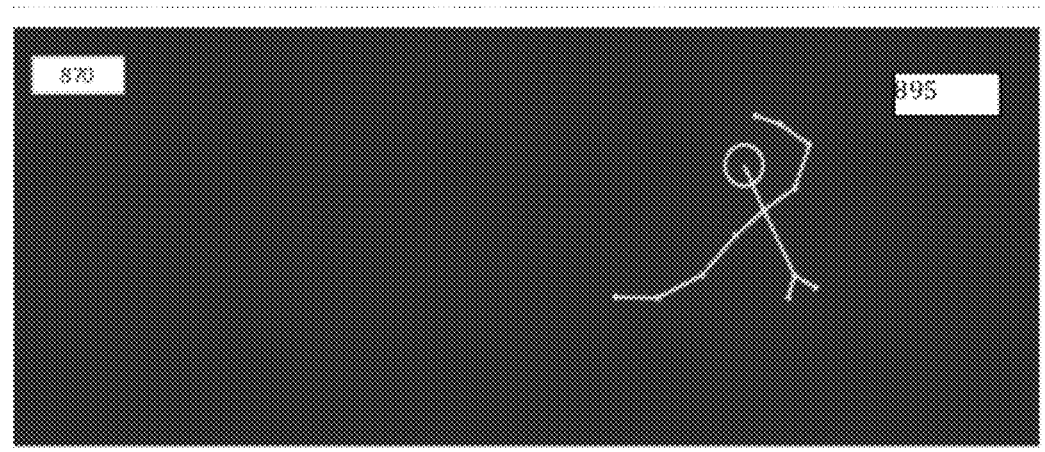

An embodiment for adding a Pilates exercise routine to the database 250 of the system 300 is depicted in FIGS. 7 and 8. In the embodiment, the Pilates exercise routine is add by recording a certified user (e.g., a trainer or instructor) performing a routine known as the "Mermaid" routine.

FIG. 7A illustrates the routine starting position frame, FIG. 7B shows a middle position frame, FIG. 7C shows the end position of the Mermaid routine from which the user moves back to the starting position through the middle position.

Each of the frames shown in FIGS. 7A, 7B and 7C provide different representations: RGB Images (740, 770, 792); Depth images (750, 780, 794); and skeletal representation (760, 790, 796). In the RGB images, the sensors (210), display (230), the Reformer (310), and a user can be identified.

The database 250 can be updated to include a plurality of frames, such as those depicted in FIGS. 7A, 7B, and 7C. The recorded frames serve as a base model. In one embodiment, only frames in a form of a skeletal model depicted in (e.g., 760, 790, 796) are saved in the database 250.

FIG. 8 is a possible screen shot describing the recording process of a Pilates routine. The frames 850, 860, 870 correspond to user postures in FIGS. 7A, 7B, and 7C. Each of frames 850, 860, 870 includes a skeleton model 880, 890 and 895 corresponding to these postures, while being recorded. Frames 850, 860, 870 are example screenshots taken from a recorder that may be provided as part of the training module. As further illustrated in FIG. 8, as part of the recording process, the training module computes and presents a table of joints and their corresponding angles around the joints. The user has the option to replay the recording, re-record a routine, and save the recording only when the user is satisfied with the results.

Figure 9:
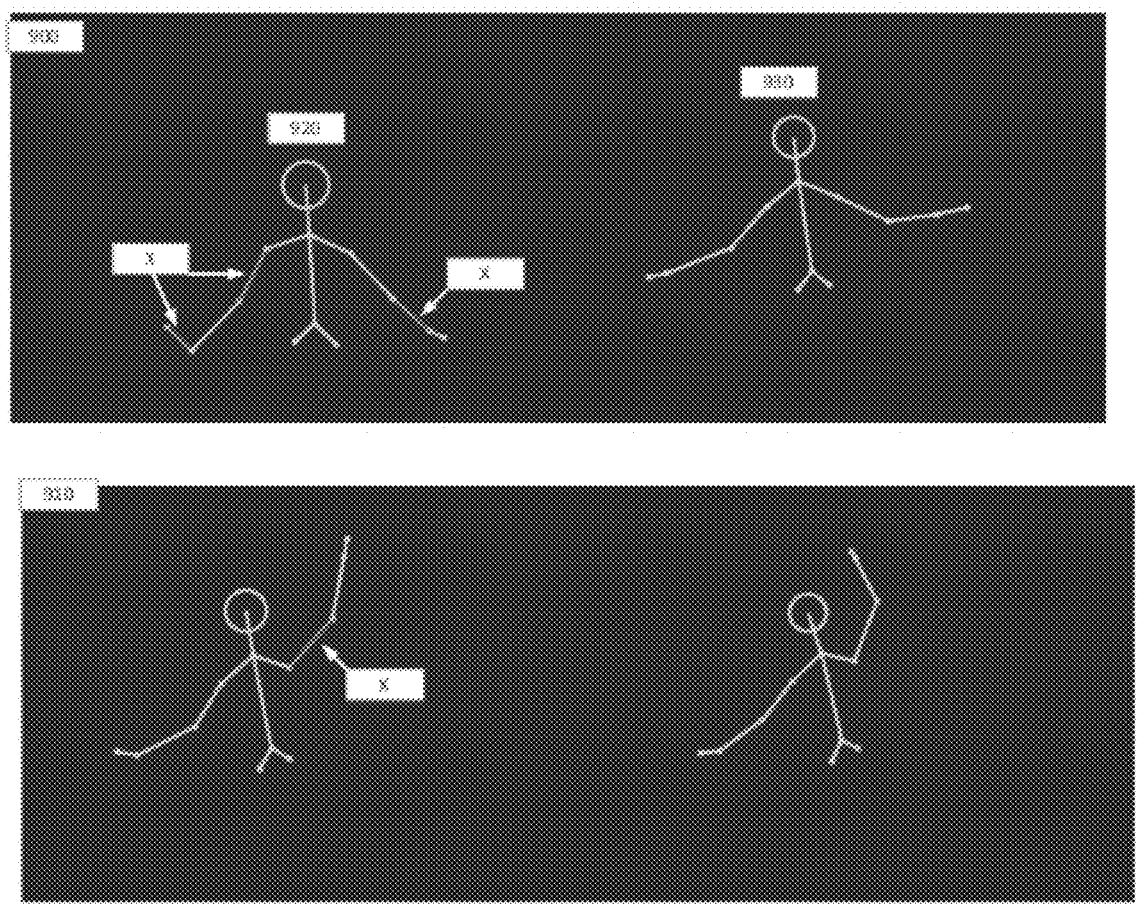
FIG. 9 shows exemplary screenshots illustrating a feedback provided to a user while performing a Pilates exercise routine.

FIG. 9 is a non-limiting example showing captured sensory data compared to the recorded routine while performing the Mermaid routine. Frames, (illustrated as screenshots) 900 and 910 are captured during different times of the execution of the routine. Frame 930 shows a skeletal model from the original recording. In an embodiment, the frame 930 is replayed to the user in order for the user to follow the displayed movement. The body parts in which the movement is not consistent with the basis model (as recoded by the trainer) are highlighted in the display (such body parts are label as X in FIG. 9).

The generation of the feedback showing the user's incorrect movement is computed by comparing the joints angle as measured during the execution of the Pilates routine compared to the base model. For example, Table 1, shows an exemplary table generated when the user is in the position shown in frame 910.

Table 1 lists a table of joints and the corresponding angles around the joints (for example, see also FIG. 5). Table 1 also lists the angle of the respective angle as recorded in the base model, and the difference between the base model angle and the user angle. In this example, the threshold for mismatch is 25 degrees, thus any angle difference higher than 25 degrees is considered as an incorrect execution of the routine.

TABLE 1

| Joint Name | Measured angle | Base model angle | Difference |
| --- | --- | --- | --- |
| Left Hand | 141.03 | 155.17 | 14.14 |
| Left Elbow | 159.9 | 134.77 | 25.12 |
| Left Shoulder | 166.38 | 162.46 | 2.39 |

Body parts that correspond to joints having an angle difference higher than the threshold trigger a feedback to the user. The feedback may include highlighting such body parts, reading out loud the name of the body part/joint which is positioned wrong, or what is required in order to perform the movement correctly ("lift your left elbow"). The feedback message can be selected according to the bone which is in the wrong posture, and the nature of the error. For example, a different message is replayed when the angle is higher than the base model angle, or when the angle is lower. The message may also be selected according to speed of exercise performance according to the requirement of the base model. A final report may be produced after performing the exercise or a series of exercises. The final report may include an ordered list of the mistakes found during the exercise routine. The report may include an ordered set of snapshots with the mistakes outlined. The report may be printed, displayed, played provided as email-message, a text message, etc.

Another possible non-limiting example for feedback, may be, the user can record the entire exercise performance and view the recording in reference or side by side to the routine recorded by trainer. This way the user can appreciate his performance after the exercise execution.

As mentioned above, in certain embodiments, a skeletal model is utilized as part of the monitoring of the user's execution of a Pilates routine performed using the Pilates Exercise device 310. However, as shown in frames 750, 780, and 794 of FIGS. 7A-7C, the Pilates exercise device is part of information captured by the sensor 210. Exercise devices including, but not limited to, Pilates exercises devices, have unique features which pose difficulties on extracting a skeletal model from a user exercising on such devices. One difficulty is caused by the fact that the user of the device is very close in space or even coupled to the exercise device. This causes immense difficulties to the processes of monitoring and identifying routines described in detail above. In fact, in many cases these processes do not achieve the desired results as the user and device are treated as a single image. Another difficulty arises from the fact that a user at his/her starting position often lays down or is viewed as being in a "non-natural" posture. In addition, during a Pilates routine there is a need to distinguish between very subtle movements such as small differences in the location of the pelvis or shoulders. The wide usage of Pilates in rehabilitation increases the need for accuracy and correctness in a skeletal model extraction and comparison.

Commercially available skeleton model extraction algorithms fail completely given these circumstances. Thus, according to an embodiment of the invention, various techniques are utilized in order to allow separation of the user image from the image the exercise device, such as a Pilates exercise device based, in part, on a skeletal model of the Pilates exercise device.

Figure 10:
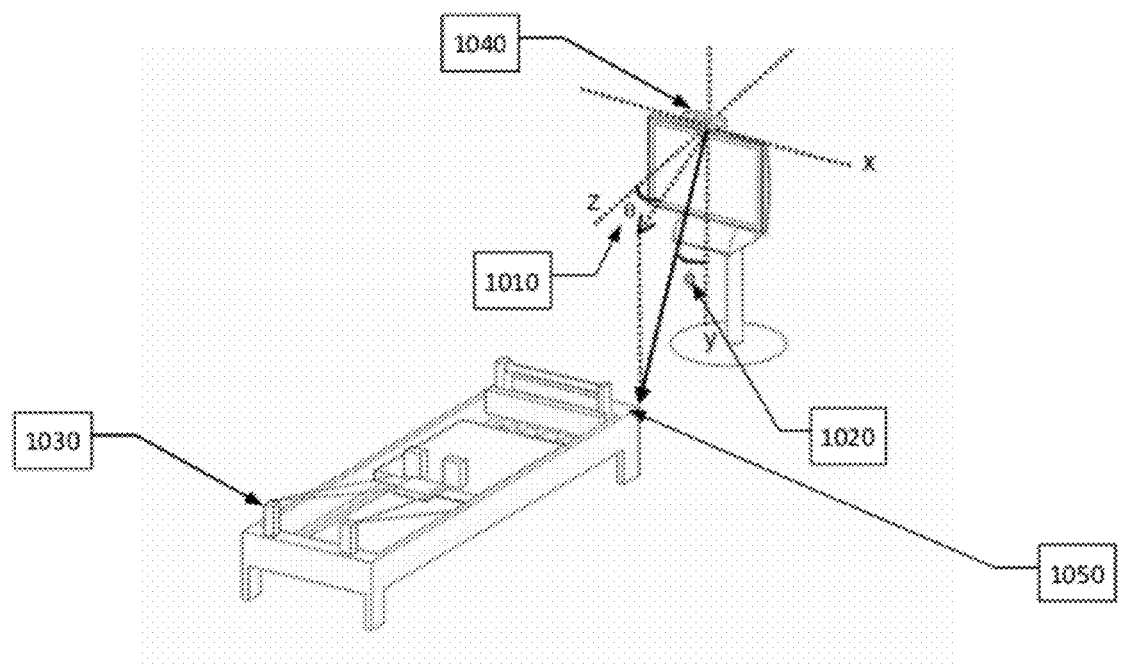
FIG. 10 is a schematic diagram utilized to describe a calibration stage for a system that includes a Pilates exercise device according to an embodiment of the invention.

In an embodiment prior to the extraction of the skeletal model of the exercise device, a calibration stage, described with reference to FIG. 10, is performed. In the calibration stage the location of the Pilates exercise device, for example, a Reformer 1030 can be identified by any array of sensors 1040. The sensors 1030 can identify the location of a pre-defined point on the non-moving part of the Reformer 1030, for example, the lower left most corner of the Reformer frame (labeled as 1050). Identification of this point can be performed, for example, using image comparison algorithms discussed in the related art. In addition, a location of a pre-defined point can be input by the user, for example, by marking on the point sensors' 1040 output image or inputting the point's coordinates. The sensors 1040 can then calculate relative angles between the sensors 1040 and the pre-defined point. These angles are marked as 1010, 1020 in FIG. 10. The angles (1010, 1020) can also be input by the user as described above. Whenever the location/position of the Reformer (1030) is changed, the calibration stage is repeated. The angles 1010, 1020 are computed during the calibration stage and can be added to the database 250.

The angles 1010, 1020 computed during the calibration stage are utilized during the monitoring and identification of exercise routines described in detailed above. Specifically, before comparing the skeletal model frames saved in the database to the skeletal model input frames of the user performing the routine, the difference in angles is calculated by subtracting the angles found in the database from the calibration stage angles. The skeletal frames in the database are then rotated in the angles' difference, so that the skeletal models can match the current position of exercise device. Such rotation can be performed, for example, using Euler Transformation or any other technique discussed in the related art.

According to another embodiment of the invention, the separation between the exercise device, e.g., a Reformer and the user can be performed by comparing a calibration image to a real-time image. Specifically, the calibration image includes sensor depth image of the exercise device and background (e.g., a room) when the user does not occupy the device. The real time frame is a depth image including the device and the exercising user. A pixel ($P_C$) from the calibration image is compared to a real time pixel ($P_{RT}$). If the case depth of these two pixels is identical, or the difference in depth falls within a certain predefined threshold, the real time pixel ($P_{RT}$), is deleted from the real time image; otherwise, the pixel ($P_{RT}$) is kept in the real time image. This process is performed on all pixels in the real-time image, and eventually a frame containing only a collection of pixels representing the exercising user is rendered.

In yet another embodiment, the calibration stage includes inputting the spatial location data of specific interest points on the exercise device. In the Reformer example such interest points may include the leg bar, the shoulder rests, the head rest, the connection point of the strap wires to the frame together with the length of the strap wires and more. The connection point of the strap wires to the frame together with the length of the strap wires can be used to calculate the possible locations in space for each strap when extended. In an embodiment, the spatial location data of interest points can be calculated by the training module 220 given that the predefined point (e.g., point 1050 of FIG. 10) location, and the exercise device's dimensions, are known to training module 220.

A method for finding the locations of bones around a joint and the angle between the bones is now described with reference to FIG. 11. A bone in the context of this disclosure is any body part participating in the exercise routine, such as legs, arms, palms, shoulders, and so on.

Figure 11A:
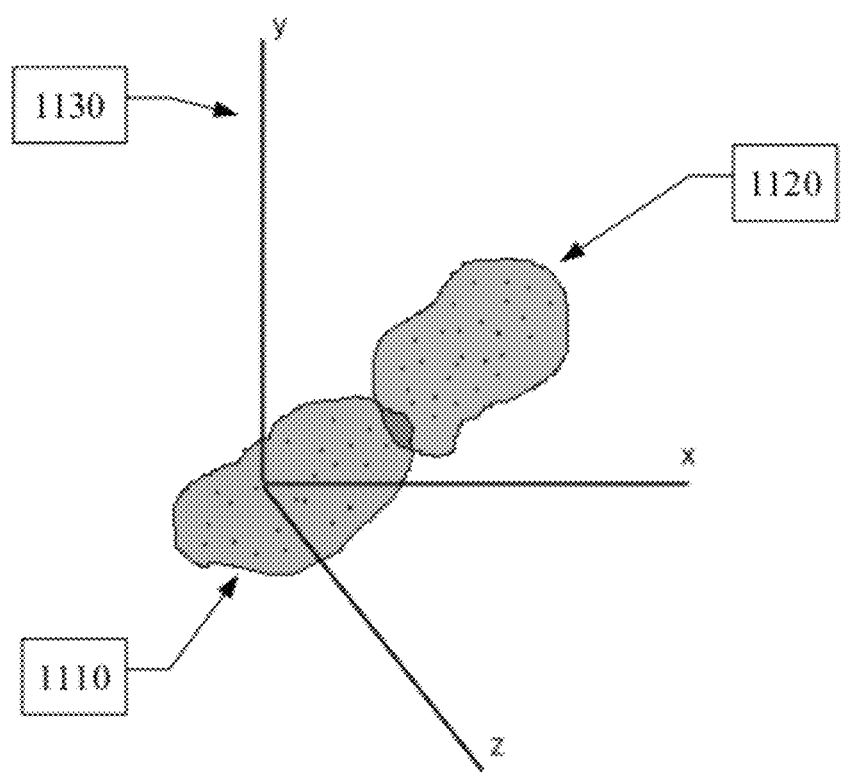
FIGS. 11A, 11B, and 11C are exemplary graphs utilized to describe a method for finding the locations of bones around a joint and the angle between the bones according to an embodiment.
Figure 11B:
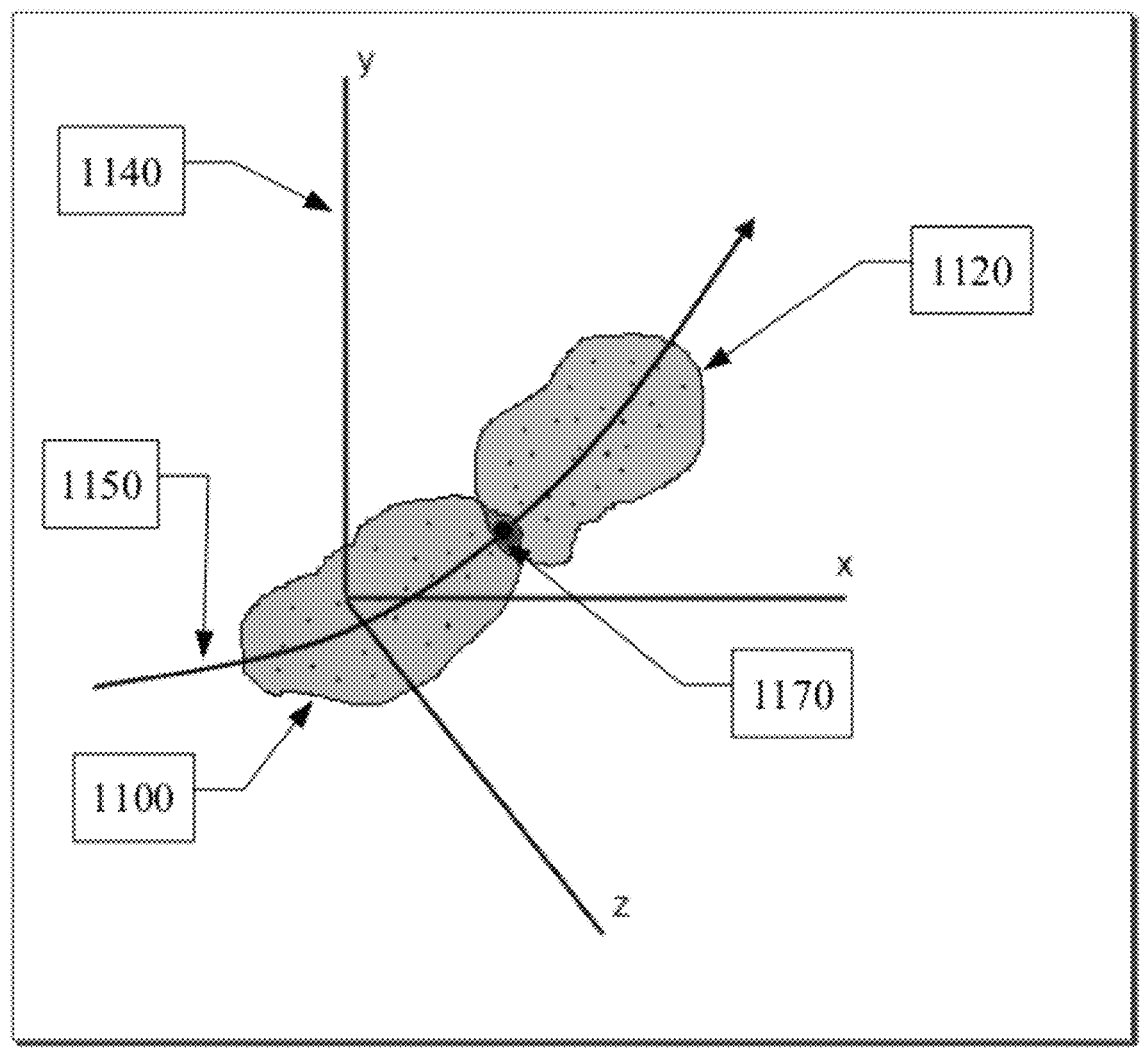

According to this method, as shown in Graph 1130 of FIG. 11A, two "clouds" of points 1110 and 1120 represent pixels belonging to two body parts (bones) around a joint. First, as shown in Graph 1140 of FIG. 11B, a parabola in space 1150 is found for the clouds of points 1110, 1120 using techniques of curve fitting, for example, a least mean squares technique. Then, the maxima/minima value of the parabola is found by deriving the found parabola equation.

Figure 11C:
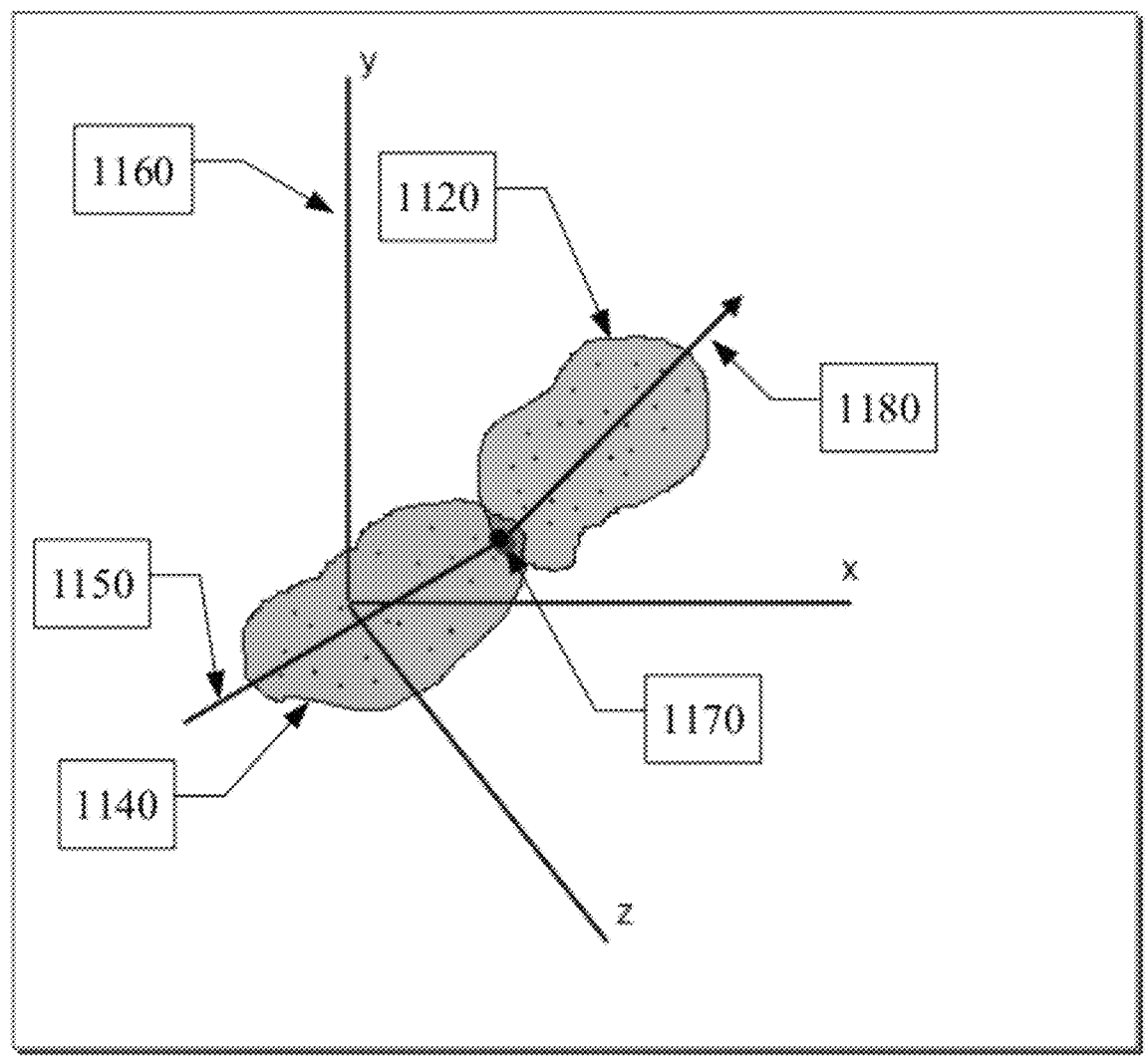

As shown in Graph 1160 of FIG. 11C, the vertex point 1170 is the Minima/Maxima of the parabola, or is a point found on the perpendicular to the parabola tangent at the Minima/Maxima point. For example, the point 1170 can be determined on the perpendicular in an equal distance from the edges of the cloud which collide with the perpendicular. The "bones" are then found by using a curve fitting technique to fit a line 1180 originating from the vertex point 1160. The angle between the lines can be measured as described in detailed above.

Building the skeletal model in the exercise comparison case (when the exercise routine being performed is known). A frame in which the user is in a known posture can be detected. For example, a start frame is either identified, as discussed above, or input by the user. The skeletal model of a known frame of an identified known exercise can be "cast" on the collection of pixels representing the user. This can be done after the skeletal model has been rotated and adjusted as described above. The cast skeletal model can be used as a starting point to find the user skeletal model.

In an embodiment, the exact location of the joints can be found as follows: for every 3 adjacent joints (joints found on 2 intersecting bones where one of them is found in the intersection point) on the starting point (cast) skeletal model, the middle joint can be deleted. The side joints can be used as limiters to isolate the two bones' clouds from the collection of pixels representing the user. The actual limit that separates these clouds can be found, for example, by making a straight line through the joint which is perpendicular to one of the two bones connected to this joint. Another method for finding this limit is by using the two straight lines through the joint which are perpendicular to the two bones connected to the joint. The limit line is the collection of points which are in the middle between these two lines.

The accurate location of the center joint can then be found according to the method described above with respect to FIG. 11. This can be repeated so that every time, the next adjacent joint's exact location is found. The process can start from one of the outer most joints, such as the leg joint. The first joint's exact location found in this case is the knee joint, the next is the lower pelvis joint and so on, until all non outer most joints' exact locations are found. The exact location of the outer most joints which do not have two neighbors can be found by: detecting a neighbor joint's exact location, and then a line from this joint to the outer joint's direction is found using a curve fitting technique. The outer joint is the edge.

Another possible technique to detect the outer most joints' location is by using the information known from the calibration stage about specific interest points on the exercise device. The intersection of these interest points with the lines found using curve fitting methods or with collection of pixels representing the user can be the outer most joints. For example, the intersection of the lines found using curve fitting with the leg bar's known location in space gives the foot joints' locations. The intersection of the collection of pixels representing the user with the sphere in space created by the possible locations of the hand straps can give the location of the outer most hand joints. In one embodiment, the locations of outer most joints are anchors used to cast the starting point skeleton model more accurately, and finding the inner joints in the process described starts from these outer most joints.

It should be noted that once the first frame skeleton model is found, the next frame model can be found using a similar method by casting the skeleton model from the corresponding frame in the database 250. The corresponding frame can be found using the time elapsed from the previous frame. Another method can be casting the previous frame found skeleton model as a starting point from the next frame. This starting point model should be close to the correct skeletal model for the next frame since the frames are close in time and space.

The various embodiments disclosed herein can be implemented as hardware, firmware, software, or any combination thereof. Moreover, the software is preferably implemented as an application program tangibly embodied on a program storage unit or non-transitory computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A system for monitoring performance of a physical exercise routine, comprising:
   a Pilates exercise device enabling a user to perform the physical exercise routine, wherein the physical exercise routine is at least a Pilates exercise routine and wherein the Pilates exercise device is any one of: a Reformer, a Pilates chair, and a Pilates Cadillac;
   a plurality of motion and position sensors for generating sensory information that includes at least position and movements of a user performing the physical exercise routine on the Pilates exercise device;
   a database containing routine information representing at least an optimal execution of the physical exercise routine;
   a training module configured to separate from sensory information at least appearance of the Pilates exercise device, compare the separated sensory information to the routine information to detect at least dissimilarities between the sensory information and the routine information, wherein the dissimilarities indicate an incorrect execution of the physical exercise routine, the training module is further configured to output a feedback to the user with at least instructions related to correcting the execution of the physical exercise routine by the user and to automatically change a tension of the Pilates exercise device based on the feedback; and
   a display for displaying the feedback.

2. The system of claim 1, wherein the training module is further configured to identify the physical exercise routine being performed.

3. The system of claim 2, wherein each of the sensory information and the routine information is represented using at least a skeletal model, wherein the skeletal model includes at least a list of joints, each joint is a connection of two adjacent body parts.

4. The system of claim 3, wherein the training module is further configured to adjust at least viewing angle of the plurality of motion and movement sensors in order to track the various body parts participating in the physical exercises routing.

5. The system of claim 3, wherein the training module is further configured to:
   compute a base angle between two body parts connected to a joint, the base angles for all body parts of a physical exercise routine are part of the routine information;
   compute a real-time angle between two body parts connected to a joint, the real-time angles for all body parts of a physical exercise routine are part of the sensory information;
   compute the difference between the base angles and real-time angles of joints participating in the physical exercise routine;
   compute a grading score based on the angles differences;
   compare the grading score to a predefined threshold; and
   generate the feedback based on a crossing of the predefined threshold.

6. The system of claim 5, wherein the grading score is computed as at least one of: an absolute value of the angles differences, a normalized value of the real-time angles differences, a sum of the angles differences, and a weighed sum of the angles differences.

7. The system of claim 6, wherein the training module is configured to separate from the sensory information at least the appearance of the Pilates exercise device by:
calculating relative angles between the sensors and a predefined point in the Pilates exercise device;
subtracting the base angles of the routine information from the relative angles; and
rotating the skeletal frames of the routine information angles difference between the base angle and the relative angle.

8. The system of claim 3, the training module is further configured to synchronize the sensory information and the routine information based, in part, on edge frames including start and end positions of the physical exercise routine.

9. The system of claim 1, wherein the training module is further configured to track a rate of movements and to count a number of physical exercise routine repetitions.

10. The system of claim 1, wherein the training module is further configured to calculate a number of burnt calories during the execution of the physical exercise routine.

11. The system of claim 1, wherein the training module is configured to separate from the sensory information the appearance of the Pilates exercise device by:
capturing a calibration depth image including the Pilates exercise device without the user;
capturing a real-time depth image including the Pilates exercise device and the user; and
comparing, pixel-by-pixel, the real-time depth image to the calibration depth image, to extract all pixels from the real-time depth image that do not represent the user.

12. A method for monitoring performance of a physical exercise routine, comprising:
receiving, by a computing device including at least a processor, sensory information from a plurality of motion and position sensors configured to track position and movement of a user performing the physical exercise routine on a Pilates exercise device, wherein the Pilates exercise device is any one of: a Reformer, a Pilates chair, and a Pilates Cadillac;
separating, by the computing device, from the sensory information at least appearance of the Pilates exercise device;
comparing, by the computing device, the separated sensory information to routine information stored in a database to detect dissimilarities between the separated sensory information and the routine information, wherein the dissimilarities indicate an incorrect execution of the physical exercise routine, wherein the routine information represents at least an optimal execution of the physical exercise routine; and
providing, by an output of the computing device, a feedback to the user, the feedback includes at least instructions related to correcting the execution of the physical exercise routine and changing a tension of the Pilates exercise device based on the feedback, wherein the physical exercise routine is at least a Pilates exercise routine.

13. The method of claim 12, further comprises:
identifying the physical exercise routine being performed.

14. The method of claim 12, wherein each of the sensory information and the routine information is represented using at least a skeletal model, wherein the skeletal model includes at least a list of joints, each joint is a connection of two adjacent body parts.

15. The method of claim 14, wherein comparing the separated sensory information to the routine information comprises:
computing a base angle between two body parts connected to a joint, the base angles for all body parts of a physical exercise routine are part of the routine information;
computing a real-time angle between two body parts connected to a joint, the real-time angles for all body parts of a physical exercise routine are part of the routine information;
computing the difference between the base angles and real-time angles of joints participating in the physical exercise routine;
computing a grading score based on the angles differences;
comparing the grading score to a predefined threshold; and
generating the feedback based on a crossing of the predefined threshold.

16. The method of claim 15, wherein separating from the sensory information at least appearance of the Pilates exercise device by:
calculating relative angles between the sensors and a predefined point in the Pilates exercise device;
subtracting the base angles of the routine information from the relative angles; and
rotating the skeletal frames of the routine information angles difference between the base angle and the relative angle.

17. The method of claim 12, wherein separating from the sensory information at least the appearance of the Pilates exercise device by:
capturing a calibration depth image including the Pilates exercise device without the user;
capturing a real-time depth image including the Pilates exercise device and the user; and
comparing, pixel-by-pixel, the real-time depth image to the calibration depth image, to extract all pixels from the real-time depth image that do not represent the user.

18. A computer software product embedded in a non-transient computer readable medium containing instructions that when executed on the computer perform a process for monitoring performance of a physical exercise routine, the process comprises:
receiving, by a computing device including at least a processor, sensory information from a plurality of motion and position sensors configured to track position and movement of a user performing the physical exercise routine on a Pilates exercise device, wherein the Pilates exercise device is any one of: a Reformer, a Pilates chair, and a Pilates Cadillac;
separating, by the computing device, from the sensory information at least appearance of the Pilates exercise device;
comparing, by the computing device, the separated sensory information to routine information stored in a database to detect dissimilarities between the separated sensory information and the routine information, wherein the dissimilarities indicate an incorrect execution of the physical exercise routine, wherein the routine information represents at least an optimal execution of the physical exercise routine; and
providing, by an output of the by the computing device, a feedback to the user, the feedback includes at least instructions related to correcting the execution of the physical exercise routine and changing a tension of the Pilates exercise device based on the feedback, wherein the physical exercise routine is at least a Pilates exercise routine.

\* \* \* \* \*